United States Patent [19]

Krnjević

[11] 4,405,610
[45] Sep. 20, 1983

[54] DRUG FOR CURING INFLAMMATORY AND/OR DEGENERATIVE AND/OR ATROPHIC MUCOUS-MEMBRANE DISEASES

[76] Inventor: Hrvoje Krnjević, A. Santica 2/II, 41.000 Zagreb, Yugoslavia

[21] Appl. No.: 247,375

[22] Filed: Mar. 25, 1981

[30] Foreign Application Priority Data

Mar. 25, 1980 [DE] Fed. Rep. of Germany ....... 3011437

[51] Int. Cl.³ ............................................ A61K 31/70
[52] U.S. Cl. .................................................. 424/180
[58] Field of Search ........................................ 424/180

[56] References Cited

U.S. PATENT DOCUMENTS 3,857,940 12/1974 Gordon ................................ 424/180

OTHER PUBLICATIONS

Chem. Abstracts 66:26722z; 83:179532p; 84:10178w.

Primary Examiner—Ethel G. Love
Attorney, Agent, or Firm—Staas & Halsey

[57] ABSTRACT

The invention relates to a pharmacuetical agent for curing inflammatory and/or degenerative and/or atrophic mucous-membrane diseases, more particularly for local application, which are characterized by the proportion of the nucleoside inoside (=hypoxanthineriboside) and of lysine orotate.

7 Claims, No Drawings

DRUG FOR CURING INFLAMMATORY AND/OR DEGENERATIVE AND/OR ATROPHIC MUCOUS-MEMBRANE DISEASES

A preferred embodiment of this drug is further characterized by a proportion of vitamin A and/or vitamin $B_{12}$ and/or folic acid.

Another preferred embodiment of the drug as provided by the invention is characterized by a proportion of vitamin A and/or thymine (=a pyrimidine base).

The drug in accordance with the teachings of the invention may also contain a skin ointment base of known composition; it is also available in gel form.

The present invention is further based on the surprising finding that the two essential ingredients inosine and lysine orotate act in synergism with each other. This synergistic effect appears strong when applied locally.

The novel drug embodying the invention is particularly effective for curing or preventing periodontitis; gingivitis (=inflammation of the gums); stomatitis aphthosa (=ucler in the oral cavity); chronic conjunctivitis (inflammation of the conjunctiva); gastritis; ulcus cruris, gastric ulcer; inflammations of the vagina region (e.g., vaginitis); fissures and rhagades, injuries to the lips of the mouth; rhinitis and skin burns.

With respect to the state of the art, it can be said that against some of the above mentioned diseases or pathological conditions, no effective drugs or remedies of any kinds are known to exist. For example, this is the case with periodontitis, and with degenerative or atrophic gingivitis.

Hitherto, no true causal drug has even been proposed for the treatment of gastritis. In the case of atrophic and degenerative vaginitis, antibiotics and other known antiinflammatory drugs have had little effect, including the broadband antibiotic oxytetracycline. Likewise, antibiotics have scarcely had any effect in combatting chapped lips.

By contrast, the drug embodying the principles of the invention cures the above mentioned pathological conditions or diseases rapidly and with lasting effects, sometimes within one night (e.g., chapped lips, bleedings in gingivitis or periodontitis, vaginitis, rhinitis). The following serves to explain the therapeutic effects:

A total of 580 Shay rats have undergone the following tests:

First, the rat stomachs were ligatured from the duodenum, cutting off any flow thereinto. In order to stop the actual gastric juice production of the rat stomachs, 2 mg atropine per rat or 10 mg cimetidine per kg rat was administered subcutaneously immediately after the duodenum (pylorus) has been ligatured.

Immediately thereafter, the drug embodying the invention was administered in the form or concentration shown in the Table, namely, dissolved in distilled water in a dose of 3 mg active substance (e.g., lysine orotate or inosine) or 1 mg active substance thymine per ml, each rat being administered a total dose of 1.5 ml. The charge was given by means of a probe or syringe and was completed in a few seconds. An hour later, 0.5 standard hydrochloric acid plus 1% pepsin was administered, in a dose of 2 ml per rat. Five hours later, the animals were killed and the stomachs examined. All the test conditions and test combinations, as well as their assessements are shown in the Table.

The assignment of marks ranges from 1, the highest mark, to 5, the lowest mark. 1 indicates that no pathological condition has been diagnosed. The assignment of marks represents a mean value of the experiment with 580 rats. In this assignment of marks, the comparative values are to compared with each other, because there are no absolutely valid values. Generally, it can be said that within 5 hours, gastric ulcers arose in varying numbers, the number of gastric ulcers being higher in older animals of both either sex, i.e., those weighing in excess of 250 g.

The accompanying Table particularly shows the synergistic effect of inosine and lysine ororate. It has been demonstrated that the control group of rats, that is to say, the animals to which the drug as provided by the invention was not administered, under otherwise identical test conditions, was about 76% less satisfactory than those treated with inosine and lysine ororate.

Another synergistic effect is apparent from a combination of lysine orotate with inosine and vitamin A as against the combination of the two ingredients lysine orotate and inosine.

TABLE

Presentation of the animal experiments involving 580 Shay rats
Curing of artificially induced gastric ulcers
Highest mark = 1, indicating absence of ulcer, the marks ranging from 1 to 5

| | Mark Mean value | |
|---|---|---|
| lysine orotate | 2.8 | Control test resulted in 76% fewer improvements |
| inosine | 3.3 | |
| lysine orotate + inosine | 2.1 | |
| control test | 3.7 | |
| lysine orotate | 2.9 | lysine orotate resulted in about 50% fewer improvements compared with the combination lysine orotate + inosine |
| lysine orotate + inosine | 2.4 | |
| lysine orotate | 3.0 | lysine orotate resulted in about 50% fewer improvements compared with the combination orotate + thymine |
| lysine orotate + thymine | 1.9 | |
| control test | 3.8 | control test resulted in 115% fewer improvements |
| lysine orotate + inosine + thymine | 1.5 | |
| lysine orotate + inosine | 2.5 | lysine orotate + inosine resulted in about 24% fewer improvements compared with the combination of the 3 ingredients |
| lysine orotate + inosine + thymine | 2.1 | |
| lysine orotate + inosine + vitamin A | 1.3 | lysine orotate + inosine resulted in about 100% fewer improvements compared with the combination lysine orotate + inosine + vitamin A |
| lysine orotate + | | |

TABLE-continued

Presentation of the animal experiments involving 580 Shay rats
Curing of artificially induced gastric ulcers
Highest mark = 1, indicating absence of ulcer,
the marks ranging from 1 to 5

| | Mark Mean value |
|---|---|
| inosine | 2.6 |

In man, the drug embodying the teachings of the invention is generally administered in a water solution.

Patients were selected who for many years had been suffering from the above diseases and had been using other known drugs, such as cimetidine, biogastrone, antiacids and sedatives.

The patients or probands suffering from gastritis or gastric ulcers received twice daily 25 mg of each active substance (lysine orotate, inosine)+vitamin of the drug embodying the invention (undiluted). The drug was usually administered in tea or undiluted milk.

Generally it can be said that already after 3 to 7 days the pains subsided and that no complications occurred. 36 probands in all were treated in this way.

In spring only two probands complained about the old discomforts, but in a weaker form.

After taking the drug of the invention again in the above mentioned quantity within two or three days twice daily, i.e., 25 mg of each active substance (lysine orotate+inosine)+vitamin, the pains subsided again.

In cases where gastric ulcers had been diagnosed (in 12 patients), the treatment lasted 3 weeks. There was only one case of resistance among 36 probands.

With respect to periodontitis, 28 probands having acute periodontitis were treated. The patients or probands suffered from bleedings of the gum when brushing their teeth, with a cyanotic or bluish discoloration of the gum and unpleasant sensation in the gum.

They received the following doses: 2 mg of each active substance (lysine orotate+inosine+vitamin) per ml water solution of the drug of the invention.

This water solution was massaged into the gum twice daily for about 20 minutes each time.

The bleedings already ceased after 48 hours. After 4 days of massaging in the above manner, also the cyanotic bluish discoloration of the gum disappeared, the therapeutic result was visible in all patients. In ten other patients, the injuries to the lips of the mouth, known as fissures and rhagades and which were extremely resistant, were treated and cured by moistening the lips twice daily for half an hour with cotton swabs dipped in the drug in the concentration specified above.

Here, too, the pathological condition disappeared after 24 to 48 hours, that is to say, the therapy succeeded.

In the case of aphthous stomatitis, 18 patients were treated who were suffering from recurrent aphthas. The drug of the invention was administered in the following doses: 3 mg of each active substance per ml (i.e., lysine orotate, inosine).

The patients were so treated that the ulcers were dabbed twice daily with swabs drenced in the drug in the concentration specified above.

Inprovement and relief occurred within 24 to 48 hours and healing occurred after 3 to 5 days.

Systematic treatment with the drug once to twice weekly for 15 minutes (it suffices to keep 2 to 3 ml of the drug only in the mouth, moving it slightly) has fully prevented a relapse of the disease. Success came about in all cases.

Furthermore, 14 patients suffering from very serious chronic conjunctivitis and who had been resistant to other drugs of known compositions were treated with the drug as provided by the invention.

Again, the above concentration: a water solution containing 1 mg of each active substance (lysine orotate+inosine)+vitamin per ml was solved in distilled water and only 1 drop was applied before bed time with a guaranteed 15-minute induction period by closing the eyes continuously for 15 minutes. After a treatment period of 6 to 14 days, the probands lost all symptoms of conjunctivitis. The therapeutic success in the case of conjunctivitis is easy to recognize in that the well-known sensation experienced by patients as if they have grains of sand in their eyes, disappeared after treatment with the drug. Eleven out of fourteen patients were completely cured after 7 to 14 days. Cosmetic application:

Tests were carried out on 40 females. A refreshing effect could already be discerned on the skin after 7 to 10 days. Tiny uneven areas of the skin and tiny folds disappeared after 3 weeks. The skin tone was enhanced. Small capillary vessels also disappeared, thereby homogenizing the skin color.

The combination of the three ingredients: lysine orotate, inosine, thymine was administered to about 30% of the patients. A slight advantage of this combination could be detected over the combination of two ingredients.

The animal tests described earlier did not involve the use of vitamin $B_{12}$ or folic acid.

The vitamin concentration was as follows:
vitamin A (water-soluble form) 250 i.u./ml or grams
$B_{12}$ 0.05 mg/ml or grams
folic acid 0.05 mg/ml or grams In all tests, thymine was administered in a dose of ¼ of the lysine orotate dose.

As a matter of precaution, reference is made to the following standard work for the chemical nomenclature used herein:

DNA Synthesis by Arthur Kornberg (Stanford University), published by W. H. Freeman and Company, San Francisco.

Preferably, the drug in accordance with the teachings of the invention is available in water-soluble, tablet or capsule form, and is preferably applied in these forms.

I claim:

1. An anti-inflammatory, degenerative, anti-atrophic drug against mucous-membrane diseases, characterized by a proportion of:
   (a) the nucleoside inosine (hypoxanthine riboside), and
   (b) lysine orotate,
   whereby 1.5 ml of a solution of the active substances with a concentration of 3 mg/ml in water is administered per 0.25 kg of body weight, by means of a syringe; or whereby two times per day 25 mg of the active substances per person are administered orally; or whereby topical treatment is carried out with a solution of 1–3 mg of the active substances per ml of water.

2. The drug as set forth in claim 1, characterized in that it contains vitamin A (water-soluble form) at 250 JU/ml or grams, and/or vitamin $B_{12}$ at 0.05 mg/ml or grams, and/or folic acid at 0.05 mg/ml or grams.

3. The drug as set forth in claim 1 or 2, characterized in that it contains vitamin A at 250 JU/ml or grams, and/or thymine (=a pyrimidine base) at ¼ of the lysine orotate dose.

4. The drug as set forth in claim 1 or 2, characterized in that it is available in gel form.

5. The drug as set forth in claim 1 or 2, characterized in that it is available in water-soluble form.

6. The drug as set forth in claim 1 or 2, characterized in that it is available as a tablet.

7. The drug as set forth in claim 1 or 2, characterized in that it is available in capsule form.

* * * * *